US009681998B2

(12) United States Patent
Nakano et al.

(10) Patent No.: US 9,681,998 B2
(45) Date of Patent: Jun. 20, 2017

(54) ABSORBENT PRODUCT WITH INTERGLUTEAL CLEFT FACING PORTION ELASTIC MEMBER

(75) Inventors: Yuki Nakano, Sakura (JP); Asami Kobori, Sakura (JP)

(73) Assignee: DAIO PAPER CORPORATION, Ehime (JP)

( * ) Notice: Subject to any disclaimer, the term of this patent is extended or adjusted under 35 U.S.C. 154(b) by 618 days.

(21) Appl. No.: 13/807,518

(22) PCT Filed: Jun. 29, 2011

(86) PCT No.: PCT/JP2011/064931
§ 371 (c)(1),
(2), (4) Date: Dec. 28, 2012

(87) PCT Pub. No.: WO2012/002443
PCT Pub. Date: Jan. 5, 2012

(65) Prior Publication Data
US 2013/0102982 A1    Apr. 25, 2013

(30) Foreign Application Priority Data

Jun. 30, 2010  (JP) ................................ 2010-149638

(51) Int. Cl.
| A61F 13/49 | (2006.01) |
| A61F 13/514 | (2006.01) |
| A61F 13/515 | (2006.01) |

(52) U.S. Cl.
CPC .. *A61F 13/49017* (2013.01); *A61F 13/49001* (2013.01); *A61F 13/49019* (2013.01); *A61F 13/515* (2013.01)

(58) Field of Classification Search
CPC .......... A61F 13/49001; A61F 13/49017; A61F 13/49019; A61F 13/515; A61F 13/49;
(Continued)

(56) References Cited

U.S. PATENT DOCUMENTS

| 6,423,042 B1 * | 7/2002 | Sasaki ............... A61F 13/49017 604/358 |
| 6,635,041 B1 * | 10/2003 | Popp ................. A61F 13/49017 604/385.24 |

(Continued)

FOREIGN PATENT DOCUMENTS

| EP | 1138302 A2 | 10/2001 |
| EP | 1184017 A1 | 3/2002 |

(Continued)

OTHER PUBLICATIONS

European Search Report of Patent Application No. 11800905.9 dated Dec. 10, 2014, 6 pages, European Patent Office.

*Primary Examiner* — Kathryn E Ditmer
(74) *Attorney, Agent, or Firm* — Renner Kenner; Arthur M. Reginelli

(57) ABSTRACT

Provided is an underpants-type disposable diaper that is improved in a fit to a part from the intergluteal cleft to the crotch of a wearer and less prone to give a wearer a puffy and discomfort feeling at a crotch portion during wearing, provided is an underpants-type disposable diaper, wherein the back body part has at an intergluteal cleft facing portion a bending fit portion which is bent so as to enter into the intergluteal cleft of a wearer.

10 Claims, 15 Drawing Sheets

(58) Field of Classification Search
CPC .......... A61F 13/49007; A61F 13/49009; A61F 13/49011; A61F 2013/49025; A61F 2013/49026; A61F 2013/49028; A61F 2013/49033; A61F 2013/49036; A61F 2013/49041
USPC ........... 604/385.01, 385.201, 385.22, 385.24
See application file for complete search history.

(56) References Cited

U.S. PATENT DOCUMENTS

| | | | |
|---|---|---|---|
| 2002/0045877 A1* | 4/2002 | Shimada | A61F 13/49011 604/385.29 |
| 2006/0264859 A1* | 11/2006 | Tsuji et al. | 604/385.28 |
| 2008/0300565 A1* | 12/2008 | Takahashi | A61F 13/15593 604/367 |
| 2008/0300568 A1* | 12/2008 | Fujioka | A61F 13/15593 604/385.27 |
| 2009/0177176 A1* | 7/2009 | Saito | 604/385.29 |
| 2010/0106123 A1* | 4/2010 | Fukae | 604/373 |

FOREIGN PATENT DOCUMENTS

| | | |
|---|---|---|
| EP | 1970036 A1 | 9/2008 |
| EP | 2011464 A1 | 1/2009 |
| EP | 2177186 A1 | 4/2010 |
| JP | 07-265357 | 10/1995 |
| JP | 09-109037 | 4/1997 |
| JP | 11-036103 | 2/1999 |
| JP | 2000-093462 | 4/2000 |
| JP | 2001-204762 | 7/2001 |
| JP | 2001-258931 | 9/2001 |
| JP | 2005278774 A * | 10/2005 |
| JP | 2006-043415 | 2/2006 |
| JP | 2007-097621 | 4/2007 |
| JP | 2007-113978 | 5/2007 |
| JP | 2008-183160 | 8/2008 |
| JP | 2008-253289 | 10/2008 |
| WO | 2004-037145 A1 | 5/2004 |
| WO | WO 2008108270 A1 * | 9/2008 |

* cited by examiner

ABSORBENT PRODUCT WITH INTERGLUTEAL CLEFT FACING PORTION ELASTIC MEMBER

This application is the national-stage application of International Application Serial No. PCT/JP2011/064931, Filed on Jun. 29, 2011, which claims the benefit of Japanese Patent Application Serial No. JP2010-149638, filed Jun. 30, 2010, which are incorporated herein by reference.

TECHNICAL FIELD

The present invention relates to an underpants-type disposable diaper having a favorably-fitting, thin, and flexible outer sheet.

BACKGROUND ART

Underpants-type disposable diapers include an outer sheet having a front body part and a back body part, and an inner body containing an absorbent body and fixed to an internal surface of the outer sheet, and the front and back body parts of the outer sheet are joined together at both side portions to form a waist opening and a pair of right and left leg openings.

In some underpants-type disposable diapers, various elastic members are fixed in a stretched state to the outer sheet for improvement of a fit to the body of a wearer (refer to Patent Literatures 1 to 7, for example). In particular, underpants-type disposable diapers including waist-portion elastic members, waist-around elastic members, and curved elastic members (represented by the members disclosed in Patent Literature 6) have a relatively high fit to the body of a wearer. The waist-portion elastic members are laterally arranged in plural and in parallel at vertical intervals therebetween at an edge portion of the waist opening. The waist-around elastic members are laterally arranged at vertical intervals therebetween in a section at a longitudinally intermediate portion side with respect to the waist-portion elastic members. The curved elastic members extend while being curved from both side portions of at least one of the front and back body parts toward the other body part with increasing proximity to a laterally intermediate position.

However, conventional general underpants-type disposable diapers have a problem of causing a puffy and discomfort feeling at a crotch portion, unlike general underpants. The inventors of the present invention have studied and revealed that one cause of this problem resides in that an absorbent body lifts from a part of the body of a wearer ranging from the intergluteal cleft to the crotch, that is, the absorbent body does not sufficiently fit the part.

To solve the foregoing problem and improve a fit to the intergluteal cleft, there have been suggested various modes in which, for example, back-side curved elastic members are arranged at a crotch traversing portion so as to project in a convex shape toward the waist opening (refer to Patent Literatures 8 and 9, for example). However, such diapers have an internal surface formed so as to fit the intergluteal cleft but are hard to maintain the fitted state, and thus are prone to provide an insufficient fit to the part from the intergluteal cleft to the crotch. In addition, at manufacture of such diapers, elastic members need to be changed in orientation at a steep angle before attachment, which makes it difficult to manufacture the diapers in high-speed lines.

CITATION LIST

Patent Literatures

Patent Literature 1: JP H7-265357 A
Patent Literature 2: JP H7-299094 A
Patent Literature 3: JP H11-36103 A
Patent Literature 4: JP 2001-258931 A
Patent Literature 5: JP 2001-204762 A
Patent Literature 6: JP 2006-043415 A
Patent Literature 7: JP 2007-113978 A
Patent Literature 8: JP 2007-97621 A
Patent Literature 9: JP 2008-253289 A

SUMMARY OF INVENTION

Technical Problem

Therefore, a main object of the present invention is to provide an underpants-type disposable diaper that is improved in a fit to a part from the intergluteal cleft to the crotch of a wearer and less prone to give a wearer a puffy and discomfort feeling at a crotch portion during wearing.

Solution to Problem

The present invention solving the foregoing problems is as follows:

An underpants-type disposable diaper, including: an outer sheet forming a front body part and a back body part; and an inner body including an absorbent body and fixed to an internal surface of the outer sheet, the front and back body parts of the outer sheet being joined at both side portions to form a waist opening and a pair of right and left leg openings, wherein the back body part has at an intergluteal cleft facing portion a bending fit portion which is bent so as to enter into the intergluteal cleft of a wearer, the outer sheet has at each of the front and back body parts a lifting elastic member which exerts a contraction force of a vertical component to lift a crotch portion toward a waist side, and a tensile stress on the front body part undergoing vertical elastic deformation is larger than a tensile stress on the back body part undergoing vertical elastic deformation.

(Operation and Effect)

Simply providing the bending fit portion does not necessarily ensure a sufficient fit to the intergluteal cleft of a wearer. However, when the front and back body parts are provided with lifting elastic members and a tensile stress on the front body part undergoing vertical elastic deformation is larger than that on the back body part, in a worn state, the crotch portion of the diaper is moved forward and lifted to fit the crotch of a wearer by a contraction force of the lifting elastic members at the front body part against a contraction force of the lifting elastic members at the back body part. Accordingly, a front end of the bending fit portion is pulled forward, and as a result, the bending fit portion fits the intergluteal cleft while maintaining the flexed state. Therefore, according to the present invention, it is possible to provide the diaper that ensures a favorable fit to the part from the intergluteal cleft to the crotch of a wearer and maintains the fit elastically following movement of the body of a wearer, which is less prone to give a wearer a puffy and discomfort feeling at the crotch portion during wearing.

The underpants-type disposable diaper according to one aspect of the invention, wherein the back body part has an intergluteal cleft-portion elastic member such that, among on the intergluteal cleft facing portion and on both side portions of the same, a lateral contraction force acts on the intergluteal cleft facing portion, and the bending fit portion is formed by the action of contraction of the intergluteal cleft-portion elastic member.

(Operation and Effect)

The bending fit portion can be formed by providing a groove or a slit in the absorbent body, but is favorably formed by providing the intergluteal cleft-portion elastic members as described above to obtain an elastic fit.

The underpants-type disposable diaper according to one aspect of the invention, wherein the intergluteal cleft-portion elastic member is an elongated elastic member that laterally extends over the intergluteal cleft facing portion, and, among at the intergluteal cleft facing portion and at both side portions of the same, the intergluteal cleft-portion elastic member is cut finely at the both side portions of intergluteal cleft facing portion such that a contraction force acts on the intergluteal cleft facing portion.

(Operation and Effect)

As in the foregoing, when the intergluteal cleft-portion elastic members are formed by the elongated elastic members extending laterally across the intergluteal cleft facing portion, the diaper can be manufactured at low costs, and at manufacture of the diaper, the intergluteal cleft-portion elastic members do not need to be changed in orientation at a steep angle as in conventional diapers. This provides an advantage of ensuring more stable manufacture of the diaper in high-speed lines.

The underpants-type disposable diaper according to one aspect of the invention, wherein a part of the intergluteal cleft facing portion under the action of a contraction force of the intergluteal cleft-portion elastic member is shaped so as to be wider in a backward direction from a front end to a longitudinal middle of the intergluteal cleft facing portion, and to be narrower in the backward direction from the longitudinal middle to a further back side of the intergluteal cleft facing portion.

(Operation and Effect)

Shaping the part of the intergluteal cleft facing portion under contraction force of the intergluteal cleft-portion elastic members in such a manner makes it possible to form the bending fit portion that favorably fits the intergluteal cleft of a wearer.

The underpants-type disposable diaper according to one aspect of the invention, wherein a groove or a slit is formed at the intergluteal cleft facing portion in the absorbent body so as to follow the intergluteal cleft of a wearer, and the bending fit portion is formed with the groove or the slit as a folding line.

(Operation and Effect)

Providing such a groove or a slit makes it possible to form the bending fit portion with a folding line at an appropriate position, and favorably maintain the shape of the bending fit portion.

The underpants-type disposable diaper according to one aspect of the invention wherein on each of the front and back body parts of the outer sheet, an elongated curved elastic member, as the lifting elastic member, is fixed so as to curve and extend toward the other body part while running from the both sides to the lateral center, in a state of being stretched in a direction of the extension at a predetermined extension ratio.

(Operation and Effect)

The curved elastic members can improve a fit to the groin of a wearer at the front body part and improve a fit to the swell of the gluteal region of a wearer at the back body part, and also favorably serves as lifting elastic members in the present invention.

The underpants-type disposable diaper according to one aspect of the invention, wherein a plurality of curved elastic members is aligned with predetermined intervals therebetween in the front and back body parts, and at portions on lateral outer sides with respect to side edges of the inner body, vertical intervals between the curved elastic members at the back body part are larger than vertical intervals between the curved elastic members at the front body part.

(Operation and Effect)

As in the foregoing, a plurality of curved elastic members is arranged at predetermined intervals therebetween such that, at the portions on the lateral outer sides with respect to the side edges of the inner body, the intervals between the curved elastic members at the back body part are relatively large and the intervals between the curved elastic members at the front body part are relatively small, whereby the diaper can ensure a fit so as to enter into the groin of a wearer by the curved elastic members at the front body part, and ensure a fit so as to cover the swell of the gluteal region of a wearer by the curved elastic members at the back body part. In addition, the diaper is less prone to cause a situation in which, when the diaper fits the intergluteal cleft of a wearer while maintaining the flexed state of the bending fit portion by the above-mentioned operation of the present invention, the diaper digs deep into the intergluteal cleft of a wearer.

The underpants-type disposable diaper according to one aspect of the invention, wherein on each of the front and back body parts of the outer sheet, a plurality of elongated waist-portion elastic members laterally extending is fixed at an edge portion of the waist opening at vertical intervals therebetween in a state of being laterally stretched at a predetermined extension ratio, and a plurality of elongated waist-around elastic members laterally extending is fixed in a section, at a longitudinally intermediate portion side with respect to the waist-portion elastic members, at vertical intervals therebetween in a state of being laterally stretched at a predetermined extension ratio.

(Operation and Effect)

When the diaper is thus configured to peripherally tighten the body of a wearer by the laterally arranged waist-portion elastic members and waist-around elastic members, it is possible to provide a sufficient peripheral tightening force and allow the curved elastic members to reliably exert a contractive action supported by the tightening force. In addition, the foregoing configuration favorably makes contraction forces of the waist elastic members and the waist-around elastic members less prone to have an adverse influence on the balanced operation of the curved elastic members.

The underpants-type disposable diaper according to one aspect of the invention, wherein the outer sheet is formed by bonding together a plurality of sheets of unwoven fabric with an adhesive at least at portions with the waist-portion elastic members, the waist-around elastic members, and the curved elastic members, and the waist-portion elastic members, the waist-around elastic members, and the curved elastic members are sandwiched and fixed between the unwoven fabric sheets, a basis weight of the outer sheet is 30 to 75 g/m$^2$, the waist-portion elastic members at the front and back body parts are 470 to 1,240 dtex in fineness, are 5 to 10 in number, have intervals of 0 to 5 mm therebetween, and have an extension ratio of 200 to 350% in a fixed state, the waist-around elastic members at the front and back body parts are 470 to 940 dtex in fineness, are 6 to 26 in number, have intervals 10 to 40 mm therebetween, and have an extension ratio of 200 to 350% in a fixed state, the curved elastic members at the front body part are 620 to 1,240 dtex in fineness, are 3 to 10 in number, have intervals 10 to 35 mm therebetween, and have an extension ratio of 230 to 380% in a fixed state that is higher than an extension ratio of the curved elastic members at the back body part, and the curved elastic members at the back body part are 620 to 1,240 dtex in fineness, are 3 to 10 in number, have intervals 10 to 35 mm therebetween, and have an extension ratio of 200 to 350% in a fixed state.

(Operation and Effect)

The present invention preferably has such elastic members in the thus structured outer sheet.

Advantageous Effects of Invention

As in the foregoing, according to the present invention, it is possible to provide advantages of improving a fit to a part from the intergluteal cleft to the crotch of a wearer and make the crotch portion less prone to give a wearer a puffy and discomfort feeling, and the like.

DESCRIPTION OF EMBODIMENTS

Figure 1:
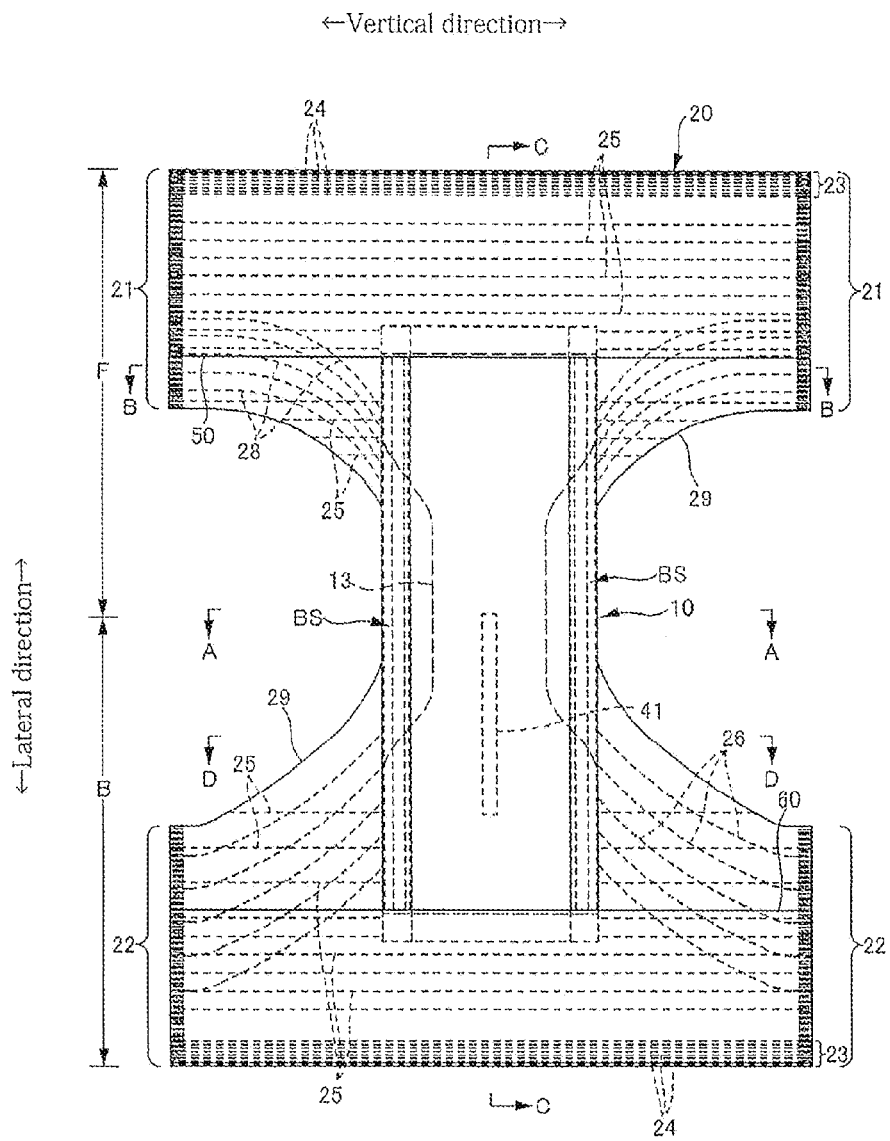
FIG. 1 is a plane view (internal surface side) of an underpants-type disposable diaper in an open state.

One embodiment of the present invention will be described below in detail with reference to the accompanied drawings.

FIGS. 1 to 11 show an underpants-type disposable diaper 1 in the embodiment. The underpants-type disposable diaper 1 (hereinafter, also referred to simply as diaper) has an outer sheet 20 forming a front body part F and a back body part B, and an inner body 10 fixed to an internal surface of the outer sheet 20 as a unit. The inner body 10 is formed by making an absorbent body 13 intervened between a liquid pervious face sheet 11 and a liquid impervious underside sheet 12. At manufacture of the diaper, an underside surface of the inner body 10 is fixed to the internal surface (upper surface) of the outer sheet 20 by joint means such as a hot-melt adhesive G, and then the inner body 10 and the outer sheet 20 are folded at a vertically (longitudinally) intermediate position as a boundary between the front body part F and the back body part B, and the front and back body parts are joined together at both side portions by thermal welding or using a hot-melt adhesive or the like to form side seal portions 21 and 22, whereby the underpants-type disposable diaper is provided with a waist opening and a pair of right and left leg openings.

(Example of Structure of Outer Sheet)

Figure 4:
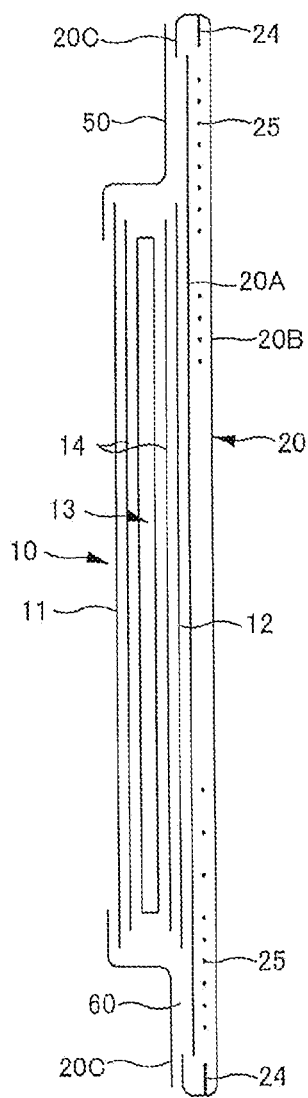
FIG. 4 is a cross section view of FIG. 1 taken along line C-C.
Figure 5:
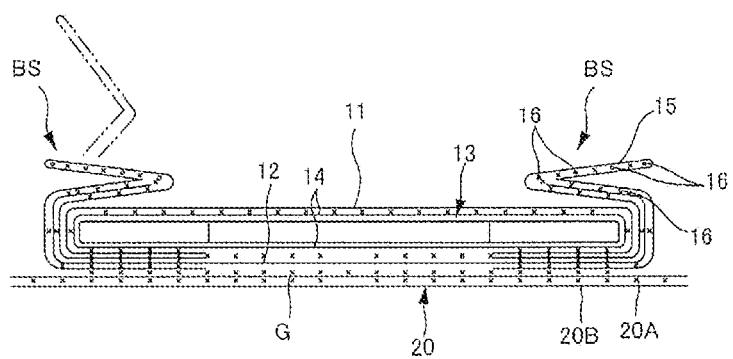
FIG. 5 is a cross section view of FIG. 1 taken along line A-A.
Figure 6:
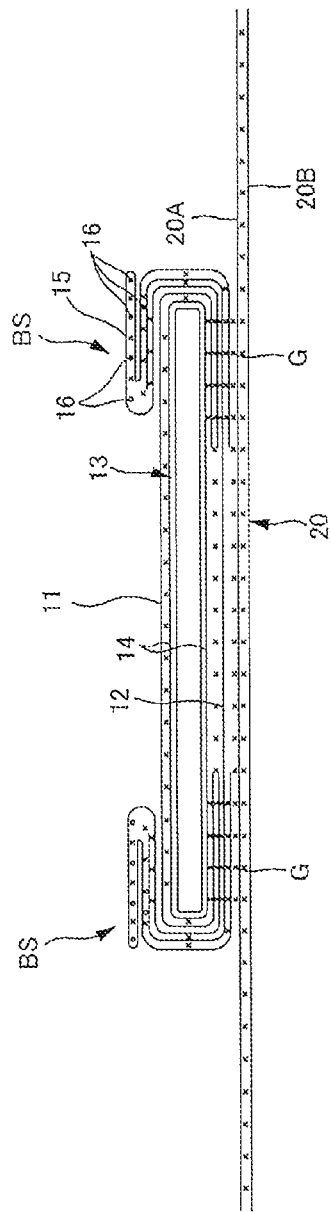
FIG. 6 is a cross section view of FIG. 1 taken along line B-B.

The outer sheet 20 is a two-layer structure unwoven fabric sheet formed by an upper layer unwoven fabric 20A and a lower layer unwoven fabric 20B (that is, the lower layer unwoven fabric constitutes an outermost unwoven fabric in this embodiment), as shown in FIGS. 4 to 6. Various elastic members are sandwiched and fixed in a stretched state to provide elasticity between the upper layer unwoven fabric 20A and the lower layer unwoven fabric 20B, and in a folded portion 20C of the lower layer unwoven fabric 20B formed by folding the lower layer unwoven fabric 20B inward at a waist opening edge. In a planar view, the outer sheet 20 is entirely shaped like a quasi-hourglass by the presence of concave leg-encircling lines 29 to form leg openings at both side portions of the center of the diaper. The elastic members may be fabricated by processing synthetic rubber or natural rubber in an arbitrary form such as threads, strings, cords, sheets, or the like.

Figure 2:
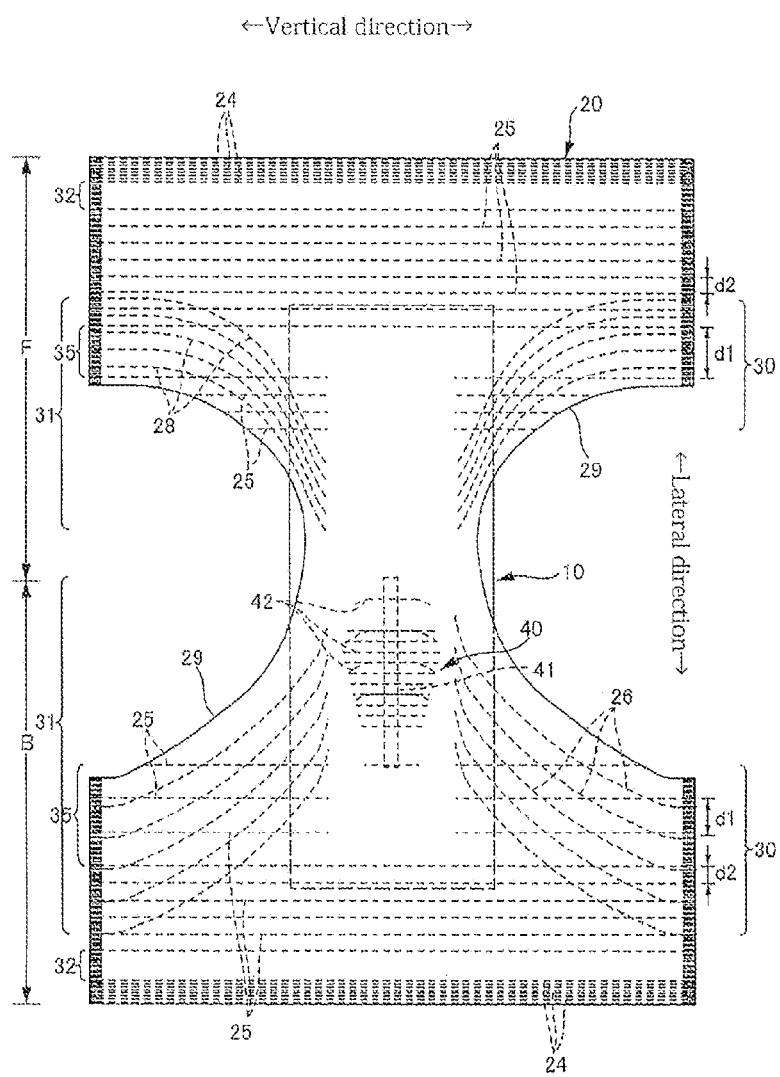
FIG. 2 is a plane view (external surface side) of the underpants-type disposable diaper in an open state.
Figure 3:
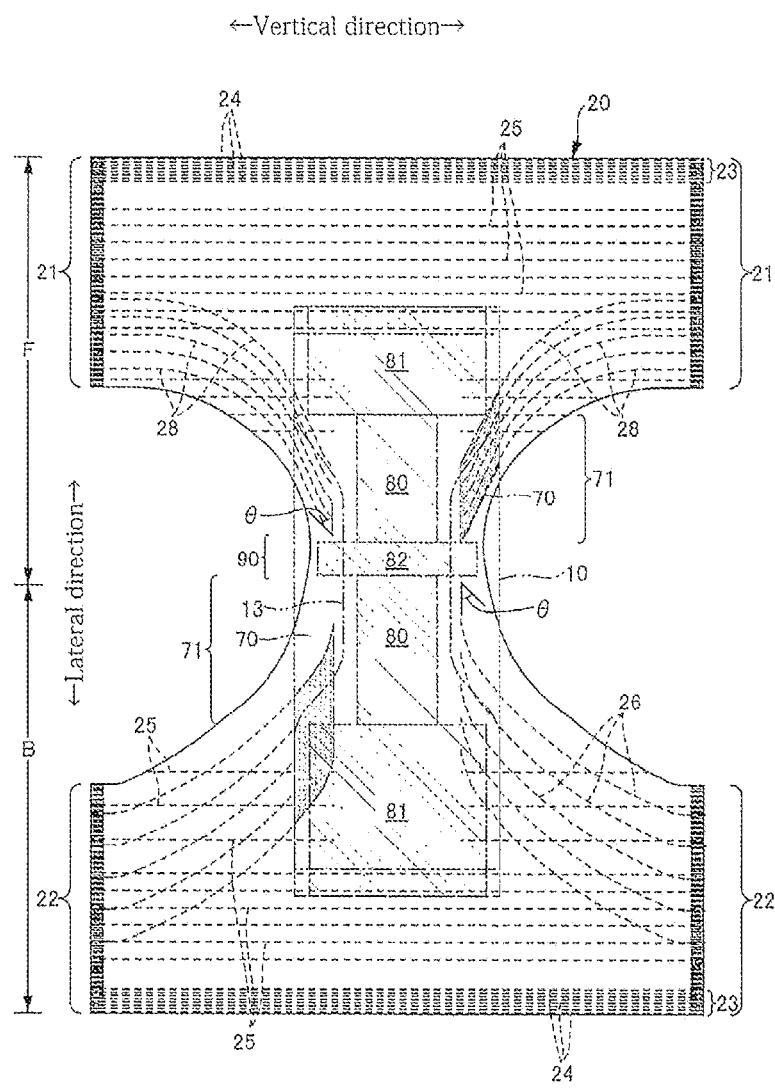
FIG. 3 is a plane view of major components of the underpants-type disposable diaper in an open state.

In particular in the outer sheet 20 of the illustrated embodiment, as shown in FIGS. 1 to 3, each of the front body part F and the back body part B includes waist-portion elastic members 24, 24, . . . arranged in the vicinity of the waist opening 23, a plurality of waist-around elastic members 25, 25, . . . laterally arranged at vertical intervals therebetween at the crotch portion side with respect to the waist-portion elastic members, a plurality of curved elastic members 26, . . . , and 28, . . . arranged separately from the waist-around elastic members 25, 25, . . . and curved from the both side seal portions 21 and 22 joining the front boy part F and the back body part B toward the laterally intermediate position so as to come closer to the other body part while extending to positions overlapping the both sides of the inner body 10 (or positions not unnecessarily overlapping the both sides, such as the vicinities of the both sides) at intervals therebetween without intersecting one another. In addition, the outer sheet 20 is not provided with leg-encircling elastic members virtually continuous from the front body part F to the back body part B along the leg-encircling lines 29, because the curved elastic members 26, . . . , and 28, . . . can provide a fit to the legs of a wearer.

However, the leg-encircling elastic members may be provided together with or instead of the curved elastic members 26, . . . and 28, . . . .

The waist-portion elastic members 24, 24, . . . are a plurality of rubber thread elastic members arranged at longitudinal intervals therebetween in the vicinity of the waist opening edge in a vertical zone including the side seal portions 21 and 22. The waist-portion elastic members 24, 24, . . . provide elasticity for tightening the diaper around the waist of a wearer, thereby allowing the waist opening edge of the diaper to attach to the body of a wearer. The waist-portion elastic members 24 use rubber threads in the illustrated embodiment, but may use tape-like elastic members, for example. In addition, the waist-portion elastic members 24, 24, . . . are sandwiched in the folded portion 20C of the lower layer unwoven fabric 20B at the waist portion, but may be sandwiched between the upper layer unwoven fabric 20A and the lower layer unwoven fabric 20B.

The waist-around elastic members 25, 25, . . . are elongated elastic members made of rubber threads or the like, that are laterally arranged at longitudinal intervals therebetween from almost upper to lower parts in a vertical zone corresponding to the side seal portions 21 and 22 and a zone at the crotch portion side with respect to the vertical zone. The waist-around elastic members 25, 25, . . . provide a lateral stretching force to the waist-around portion of the front body part F and the back body part B to allow the diaper to attach to the body of a wearer. In addition, the boundary between the waist-portion elastic members 24, 24, . . . and the waist-around elastic members 25, 25, . . . may not be necessarily clear. For example, of the elastic members laterally arranged at longitudinal intervals therebetween at the front body part F and the back body part B, some elastic members on the upper side may serve as waist-portion elastic members and the remaining elastic members may serve as waist-around elastic members, even though the exact numbers may not be specified.

At the back body part B, the back-side curved elastic members 26, 26, . . . arranged separately from the waist-around elastic members 25, 25, . . . have a minimum point at which a smaller angle θ formed by intersecting with the vertical direction is minimum at a longitudinally intermediate position (hereinafter, also referred to as vertically intersecting angle). In addition, the back-side curved elastic members 26, 26, . . . are arranged in a predetermined curve that has the vertically intersecting angle θ increasing within the range of 0 to 90 degrees with increasing proximity to both lateral sides from the minimum point and has an intersecting portion 70 at which the vertically intersecting angle θ is 60° or less in a section overlapping both sides of the inner body 10 when the diaper is opened. The number of the back-side curved elastic members 26 may be one but is preferably more than one. In the illustrated example, the back-side curved elastic members 26, 26, . . . are five rubber thread elastic members that are arranged at intervals therebetween without intersecting one another. The back-side curved elastic members 26, 26, . . . are not arranged in a virtually bundle of about two or three resilient and elastic members at close intervals therebetween but are arranged in plural at predetermined intervals therebetween so as to form a predetermined stretching zone.

At the front body part F of the outer sheet 20, the ventral-side curved elastic members 28, 28, . . . arranged separately from the waist-around elastic members 25, 25, . . . also have a minimum point at which the vertically intersecting angle θ formed by intersecting with the vertical direction is minimum at a longitudinally intermediate position. In addition, the ventral-side curved elastic members 28, 28, . . . are arranged in a predetermined curve that has the vertically intersecting angle θ increasing within the range of 0 to 90 degrees with increasing proximity to both lateral sides from the minimum point and has an intersecting portion 70 at which the vertically intersecting angle θ is 60° or less in a section overlapping the both sides of the inner body 10 when the diaper is opened. The number of ventral-side curved elastic members 28, 28, . . . may be one but is preferably more than one. In the illustrated example, the ventral-side curved elastic members 28, 28, . . . are five thread elastic members that are arranged at intervals therebetween without intersecting one another. The ventral-side curved elastic members 28, 28, . . . are not arranged in a virtually bundle of about two or three resilient and elastic members at close intervals therebetween but are arranged in plural at predetermined intervals therebetween so as to form a predetermined stretching zone.

The curved elastic members 26, . . . and 28, . . . may not be entirely curved but may have straight portions unlike in the illustrated example. If the curved elastic members 26, . . . and 28, . . . are to be provided at both the front body part F and the back body part B, some or all of the curved elastic members arranged at the front body part F and some or all of the curved elastic members B arranged at the back body part B may intersect one another at the crotch portion or near the front or back side of the crotch portion (not illustrated). However, preferably as in the illustrated example, the curved elastic members 28 arranged at the front body part F and the curved elastic members B arranged at the back body part B, are vertically separated at the longitudinally intermediate position, in particular, at a position slightly nearer the front body part F, without intersecting one another. In this arrangement, preferably, a minimum vertical separation distance is about 10 to 20 mm in a vertical separation zone 90, and a wide fixed section described later is provided at the vertical separation zone 90.

Figure 8:
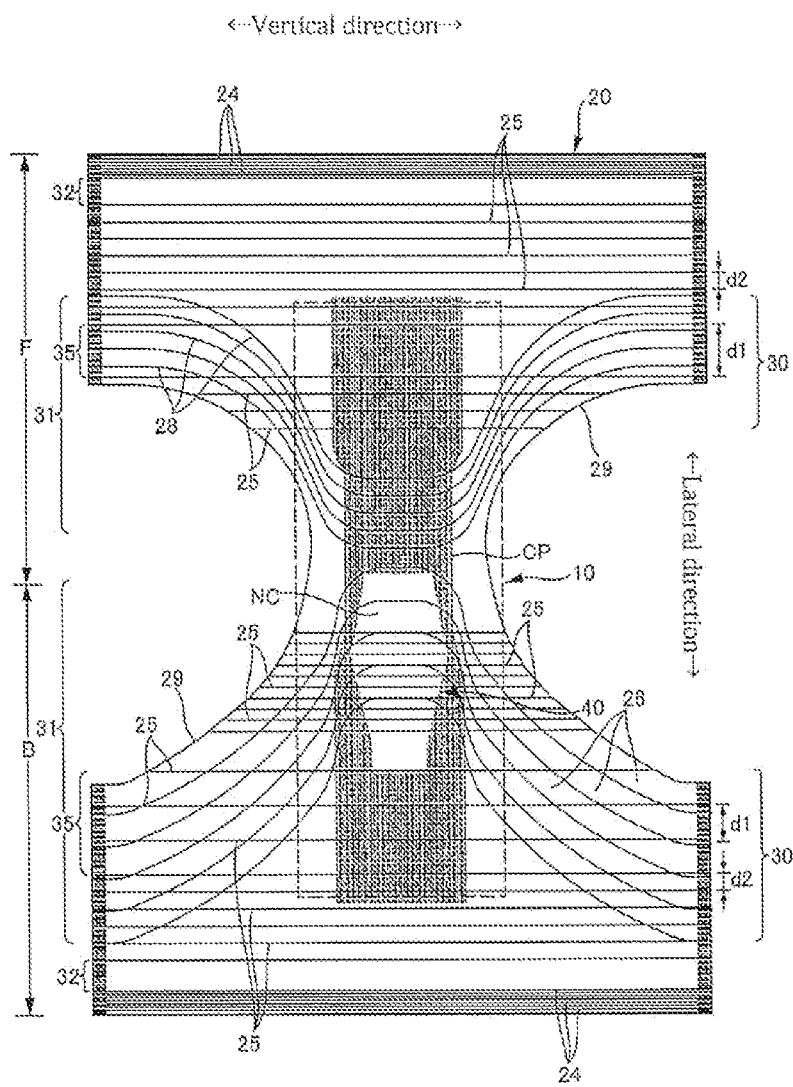
FIG. 8 is a plane view of an elastic member cutting pattern.
Figure 9:
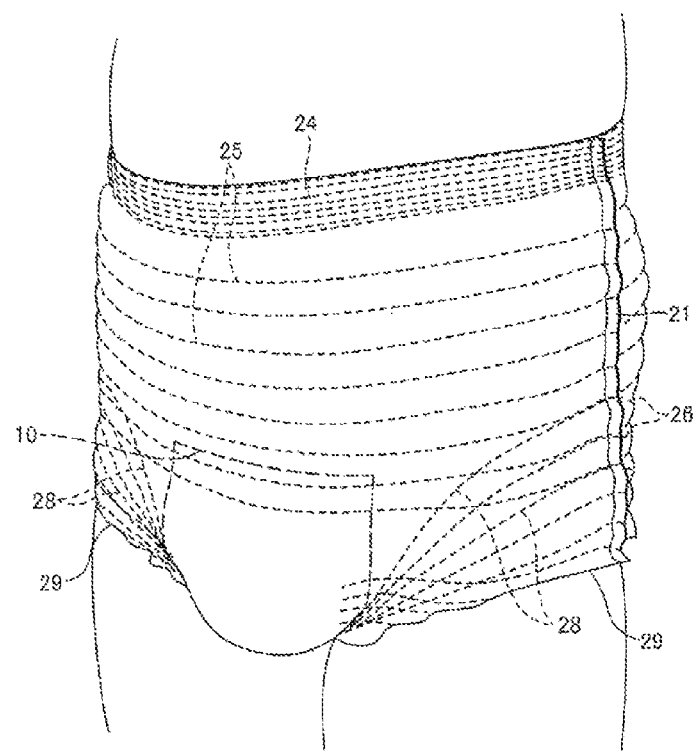
FIG. 9 is a perpendicular view of the underpants-type disposable diaper in a worn state.
Figure 10:
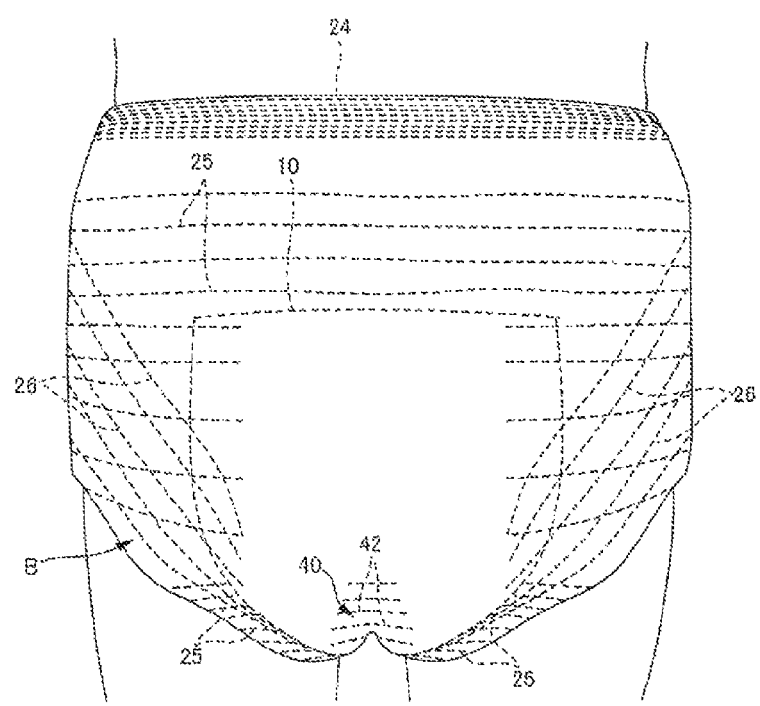
FIG. 10 is a back side view of the underpants-type disposable diaper in a worn state.

Meanwhile, in the illustrated example, the waist-around elastic members 25, 25, . . . and the curved elastic members 26, . . . and 28, . . . arranged at the front body part F and the back body part B are not provided at a portion of the diaper crossing over the inner body 10, and the portion is set as a non-stretched section. As in the foregoing, in examples of the diaper with no elastic members, no elastic members exist or some elastic members exist but are finely cut so as not to exert a contraction force. FIG. 8 shows the latter example in which the waist-around elastic members 25, 25, . . . and the curved elastic members 26, . . . and 28, . . . are continuously provided so as to cross over the inner body 10 from the side portion joining edge 22 on one side to the side portion joining edge 22 on the other (opposite) side, and then some or all of the elastic members crossing over the inner body 10 are cut in a predetermined cutting pattern CP to make the elastic members discontinuous. By making the elastic members 25, 26, and 28 discontinuous at portions overlapping the inner body 10, it is possible to prevent lateral contraction of the inner body 10 (in particular, the absorbent body 13). As a matter of course, the waist-around elastic members 25, 25, . . . and the curved elastic members 26, . . . and 28, . . . may be continuously arranged across the inner body 10.

The outer sheet 20 described above can be manufactured using techniques disclosed in JP H4-28363 A and JP H11-332913 A, for example. In addition, the curved elastic members 26, . . . and 28, . . . can be preferably cut and made discontinuous on the inner body 10 by cutting methods disclosed in JP 2002-35029 A, JP 2002-178428 A, and JP 2002-273808 A.

(Bending Fit Portion)

Figure 11:
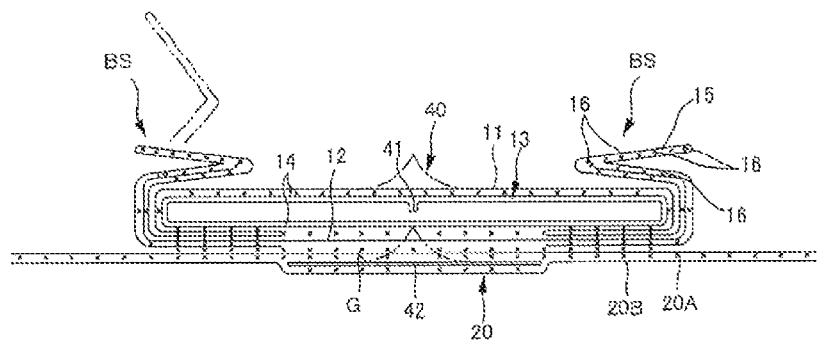
FIG. 11 is a cross section view of FIG. 1 taken along line D-D.

Characteristically, as shown in FIG. 11, a bending fit portion 40 is provided at the intergluteal cleft facing portion of the back body part B so as to be bent and entered into the intergluteal cleft of a wearer. A portion in FIG. 11 shown by two-dot chain lines constitutes the bending fit portion 40 in a bending state. The bending fit portion 40 can also be formed by providing a vertical groove 41 or a vertical slit at the intergluteal cleft facing portion of the absorbent body 13. In this case, the bending fit portion 40 can be formed with a folding line at an appropriate position and be easy to maintain the shape. In addition to or instead of this, intergluteal cleft-portion elastic members 42 may be provided to, among at the intergluteal cleft facing portion and at portions on both sides of the intergluteal cleft facing portion at the back body part B, exert a lateral contraction force on the intergluteal cleft facing portion, so that the bending fit portion 40 is formed by contractive action of the intergluteal cleft-portion elastic members 42. This makes it possible to elastically maintain the shape of the bending fit portion 40 in a favorable manner.

The intergluteal cleft-portion elastic members 42 may be formed by providing dedicated elastic members at a predetermined portion of the back body part B, or may be formed by using, together with or instead of the dedicated elastic members, some of the waist-around elastic members 25 and the curved elastic members 26, . . . laterally crossing over the intergluteal cleft facing portion. In the case of providing the dedicated elastic members, the dedicated elastic members may be elongated elastic members made of rubber threads or the like or sheet-like elastic members.

In the illustrated example, some of the curved elastic members 26, . . . and the waist-around elastic members 25 at the back body part B are used as intergluteal cleft-portion elastic members 42. More specifically, as shown in FIG. 8, a large number of waist-around elastic members 25 is continuously provided at the back body part B in the lateral direction so as to pass through the intergluteal cleft facing portion of the outer sheet 20, and the curved elastic members 26, . . . are continuously provided such that some (or all) of the members curved toward the crotch portion laterally cross over the intergluteal cleft facing portion, and then the elongated elastic members 25, . . . and 26, . . . positioned on the both sides of the intergluteal cleft facing portion are finely cut in the predetermined cutting pattern CP, and the elongated elastic members 25, . . . and 26, . . . positioned at the intergluteal cleft facing portion are not cut but are left as non-cut portions. The non-cut elastic members serve as intergluteal cleft-portion elastic members 42 to exert a lateral contraction force on the intergluteal cleft facing portion at the back body part B to allow the intergluteal cleft facing portion to be bent and bulged in a peak shape on an internal surface.

The portion of the outer sheet 10 under the action of the contraction force of the intergluteal cleft-portion elastic members 42 may be shaped in a rectangle extending in the longitudinal direction or may be shaped so as to become wider with increasing proximity to the front side (for example, an isosceles triangle with the bottom side positioned at the front side or a trumpet shape with two equal curved sides). Preferably, the portion is shaped so as to become wider with increasing proximity to the back side from the front end to the longitudinally intermediate position of the intergluteal cleft facing portion and become narrower with increasing proximity to the back side at the further back portion, thereby to form the bending fit portion 40 so as to preferably fit in particular the intergluteal cleft of a wearer.

Dimensions of the portion of the outer sheet 10 under the action of the contraction force of the intergluteal cleft-portion elastic members 42 (the portion of the outer sheet 10 having the intergluteal cleft-portion elastic members 42) may be decided as appropriate. Desirably, the portion has a width narrower than that of the absorbent body 13, for example, within the range of 40 to 90 mm, and has a front-back length of about ⅕ to ½ of the front-back length of the absorbent body 13. In addition, the portion preferably has a front end at the longitudinal intermediate position or in the vicinity of the same. The non-cut portion NC in the foregoing cutting pattern is the same in shape as the portion under the action of the contraction force, and is the same in size as or slightly larger than the portion under the action of the contraction force. In addition, the groove 41 or the slit provided in the absorbent body 13 may have a front-back length and a width that may be smaller or larger than or the same as those of the portion under the action of the contraction force, but preferably has a width that is smaller than that of the portion under the action of the contraction force.

(Balance in Tensile Stress on Vertical Elastic Deformation)

Characteristically, the curved elastic members 26, . . . and 28, . . . are provided at the front body part F and the back body part B, as lifting elastic members exerting contraction forces of vertical components so as to lift the crotch portion toward the waist. In addition, the contraction forces are balanced between the front and back sides such that a tensile stress on the front body part F undergoing vertical elastic deformation is larger than a tensile stress on the back body part B undergoing vertical elastic deformation. The tensile stress on each of the body parts undergoing elastic deformation can be measured by separating the both side seal portions 21 and 22 of the diaper to open the diaper; holding the waist opening edge of the body part to be measured and the crotch side end of the other body part not to be measured by grips of a tensile testing machine; and subjecting the body part to be measured to tensile testing. A difference in tensile stress between the body parts undergoing elastic deformation can be set as appropriate. Preferably, the tensile stress on the front body part F undergoing vertical elastic deformation while being stretched by 80%, is about 1.1 to 1.2 times that on the back body part B.

Figure 12:
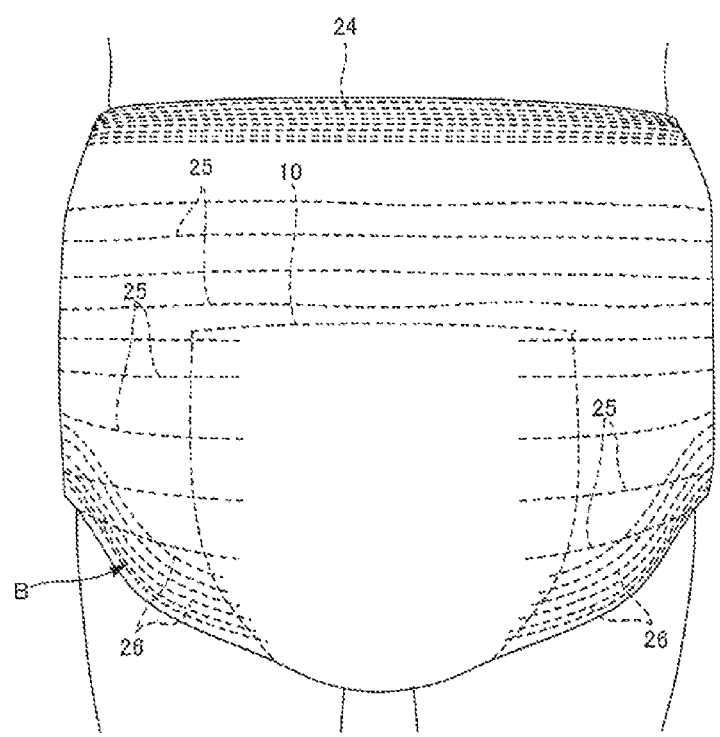
FIG. 12 is a back side view of a conventional underpants-type disposable diaper in a worn state.

When the lifting elastic members 26, . . . and 28, . . . are provided at the front body part F and the back body part B and the tensile stress on the front body part F undergoing vertical elastic deformation is made larger than that on the back body part B as described above, as shown in FIGS. 10 and 11, the crotch portion of the diaper in a worn state is moved forward and lifted by the contraction force of the lifting elastic members 28, . . . at the front body part F the contraction force of the lifting elastic members 26, . . . at the back body part B so as to fit the crotch of a wearer. Accordingly, the front end of the bending fit portion 40 is pulled forward, and as a result, the bending fit portion 40 fits the intergluteal cleft of a wearer while maintaining the bent state. Therefore, the diaper favorably fits the body of a wearer ranging from the intergluteal cleft to the crotch, and elastically maintains the fit to follow movement of a wearer, which is less prone to give a wearer a puffy and discomfort feeling at the crotch portion during wearing. In contrast, in a conventional general underpants-type disposable diaper, the intergluteal cleft facing portion is bulged and largely separated from the skin of a wearer as shown in FIG. 12, and as a result, the diaper gives a wearer a puffy and discomfort feeling at the crotch portion, thereby bringing about a significant unpleasant sensation not caused by general underpants.

In the illustrated example, the lifting elastic members are formed only by the curved elastic members 26, . . . and 28, . . . . The curved elastic members 26, . . . and 28, . . . perform the functions of improving a fit to the groin of a wearer at the front body part F and improving a fit to the swell of the gluteal region of a wearer at the back body part B. As a matter of course, instead of or together with the curved elastic members 26, . . . and 28, . . . , elongated or sheet-like elastic members may be vertically fixed in a stretched state at the laterally intermediate position to form the lifting elastic members (not illustrated). If the curved elastic members 26, . . . and 28, . . . are to be used in combination with other kinds of lifting elastic members, the curved elastic members 26, . . . and 28, . . . may be provided only one of the front body part F and the back body part B, and the other lifting elastic members may be provided at the other body part, unlike in the illustrated example.

In particular, if the curved elastic members 26, . . . and 28, . . . are provided as in the illustrated example, the vertical intervals between the curved elastic members 26 at the back body part B are preferably larger than the vertical intervals between the curved elastic members 28 at the front body part F on lateral outer sides with respect to the side edges of the inner body 10. In this case, the diaper provides a fit so as to enter into the groin of a wearer by the presence of the curved elastic members 28 at the front body part F, and provides a fit so as to cover the swell of the gluteal region of a wearer by the presence of the curved elastic members 26 at the back body part B. In addition, when the bending fit portion 40 fits the intergluteal cleft of a wearer while maintaining a bent state, the bending fit portion 40 is less prone to dig deep into the intergluteal cleft of a wearer.

The foregoing front-back contraction force balance can be realized by differentiating at least one of factors for a tensile stress on each of the body parts F and B undergoing vertical elastic deformation, for example, at least one of fineness, extension ratio, number, and the like of the lifting elastic members 26, . . . and 28, . . . between the body parts F and B. To adjust the fineness or the like of the lifting elastic members 26, . . . and 28, . . . , it is preferred to determine the number of the lifting elastic members 26, . . . and 28, . . . in accordance with the size and layout of the diaper. Accordingly, it is preferred to set at least one of the fineness and the extension rate so as to be thicker or higher at the front body part F than at the back body part B, on the basis of the layout and the number, thereby to obtain the foregoing front-back contraction force balance.

Specifically, in the illustrated example, the specifications for the components of the diaper are preferably defined within the following ranges. Here, the elastic members are measured in fineness by the unified unit of dtex, but a material for the elastic members is not limited to synthetic rubber but may be natural rubber. In the case of using natural rubber, the unit dtex refers to fineness of natural rubber having an SS curve that is equivalent to that of synthetic rubber measured in the unit of dtex (e.g.: a fineness of 0.5 to 3.0 mm if natural rubber is used for the waist-portion elastic members 24).

Outer sheet 20
  Material: Unwoven fabric
  Basis weight: 30 to 75 g/m², in particular 36 to 60 g/m²
Waist-portion elastic members 24 at the front body part F and the back body part B
  Fineness: 470 to 1,240 dtex, in particular 940 to 1,240 dtex
  Number: 5 to 10, in particular 8 to 10 (each of the body parts)
  Interval: 0 to 5 mm, in particular 3 to 5 mm
  Extension ratio in fixed state: 200 to 350%, in particular 250 to 300%
Waist-around portion elastic members 25 at the front body part F
  Fineness: 470 to 1,240 dtex, in particular 470 to 620 dtex
  Number: 6 to 26, in particular 8 to 16
  Interval: 10 to 40 mm, in particular 15 to 35 mm
  Extension ratio in fixed state: 200 to 350%, in particular 250 to 300%
Waist-around portion elastic members 25 at the back body part B not constituting the intergluteal cleft-portion elastic members 42
  Fineness: 470 to 1,240 dtex, in particular 470 to 620 dtex
  Number: 6 to 24, in particular 9 to 14
  Interval: 10 to 40 mm, in particular 15 to 35 mm
  Extension ratio in fixed state: 200 to 350%, in particular 250 to 300%
Waist-around portion elastic members 25 at the back body part B constituting the intergluteal cleft-portion elastic members 42
  Fineness: 470 to 1,240 dtex, in particular 940 to 1,240 dtex
  Number: 5 to 20, in particular 9 to 10
  Interval: 5 to 20 mm, in particular 10 to 16 mm
  Extension ratio in fixed state: 200 to 350%, in particular 250 to 330%
Curved elastic members 28 at the front body part F
  Fineness: 620 to 1,240 dtex, in particular 620 to 940 dtex
  Number: 3 to 10, in particular 5 to 10
  Interval: 10 to 35 mm, in particular 16 to 32 mm
  Extension ratio in fixed state: 230 to 380%, in particular 300 to 380% and higher than that of the curved elastic members 26 at the back body part B
Curved elastic members 26 at the back body part B (including members constituting the intergluteal cleft-portion elastic members 42)
  Fineness: 620 to 1,240 dtex, in particular 620 to 940 dtex
  Number: 3 to 10, in particular 5 to 10
  Interval: 10 to 35 mm, in particular 16 to 32 mm
  Extension ratio in fixed state: 200 to 350%, in particular 250 to 300%
(Configuration Related to Flexibility of Outer Sheet)

The outer sheet 20 is preferably configured such that: there is a partial (or entire) overlap between a vertical zone of the outer sheet 20 with the waist-around elastic members 25 . . . and a vertical zone 31 of the outer sheet 20 with the curved elastic members 26, . . . and 28, . . . ; a plurality of (for example, about 5 to 10) waist-around elastic members 25 . . . is included in the overlapping zone 30; and intervals d1 between at least some of the included waist-around elastic members 25 . . . are larger than intervals d2 between the other waist-around elastic members 25 . . . . In addition, the outer sheet 20 is preferably configured such that, out of the overlapping zone 30, a plurality of (for example, about 10 to 16) waist-around elastic members 25 . . . is provided in an intermediate zone 32 between the vertical zone 31 with the curved elastic members 26, . . . and 28, . . . and a vertical zone with the waist-portion elastic members 24.

As in the foregoing, when the overlapping zone 30 is allowed for to an extent between the vertical zone with the waist-around elastic members 25 . . . and the vertical zone with the curved elastic members 26, . . . and 28, . . . and a portion is provided within the overlapping zone 30 such that the waist-around elastic members 25 . . . are arranged at larger intervals therebetween, it is possible to suppress close arrangement of the elastic members without deteriorating a fit. As a result, the outer sheet 20 has pleats not closely spaced in the overlapping zone 30, which makes it possible to suppress unnecessary increase in thickness, hardening of the elastic members due to properties thereof and adhesion thereof, thereby obtaining a soft and comfortable wearing feeling.

In normal cases, preferably, the intervals d1 between the waist-around elastic members 25 . . . are about 15 to 50 mm, and the intervals d2 between the other waist-around elastic members 25 . . . are about 10 to 20 mm. In addition, the vertical length of the overlapping zone 30 is preferably about 15 to 30% of the entire length of the diaper in an open state, and the proportion of a portion 35 with larger intervals between the waist-around elastic members 25 . . . in the overlapping zone 30 is preferably about 60 to 100% of the overlapping zone 30 with respect to the vertical length (that is, the total sum of the intervals d1/the vertical length of the overlapping zone 30). If the overlapping zone 30 is too narrow, there is less significance in increasing the intervals between the waist-around elastic members 25 . . . . If the overlapping zone 30 is too wide, the portion 35 with the larger intervals between the waist-around elastic members 25 . . . becomes large to deteriorate a fit. In addition, if the proportion of the portion 35 with the larger intervals between the waist-around elastic members 25 . . . in the overlapping zone 30 is too small, the diaper can be expected to be improved in flexibility in part but not in a sufficient level.

Specifically, in the illustrated example, the proportion of the portion 35 with the larger intervals d1 between the waist-around elastic members 25 . . . in the overlapping zone 30 is about 40% at the front body part F and 100% at the back body part B. As in the foregoing, the configuration of the outer sheet 20 related to improvement in flexibility can vary between the front body part F and the back body part B, or may be applied to only either of the front body part F and the back body part B in the outer sheet 20 (the same also applies to the following descriptions).

Figure 7:
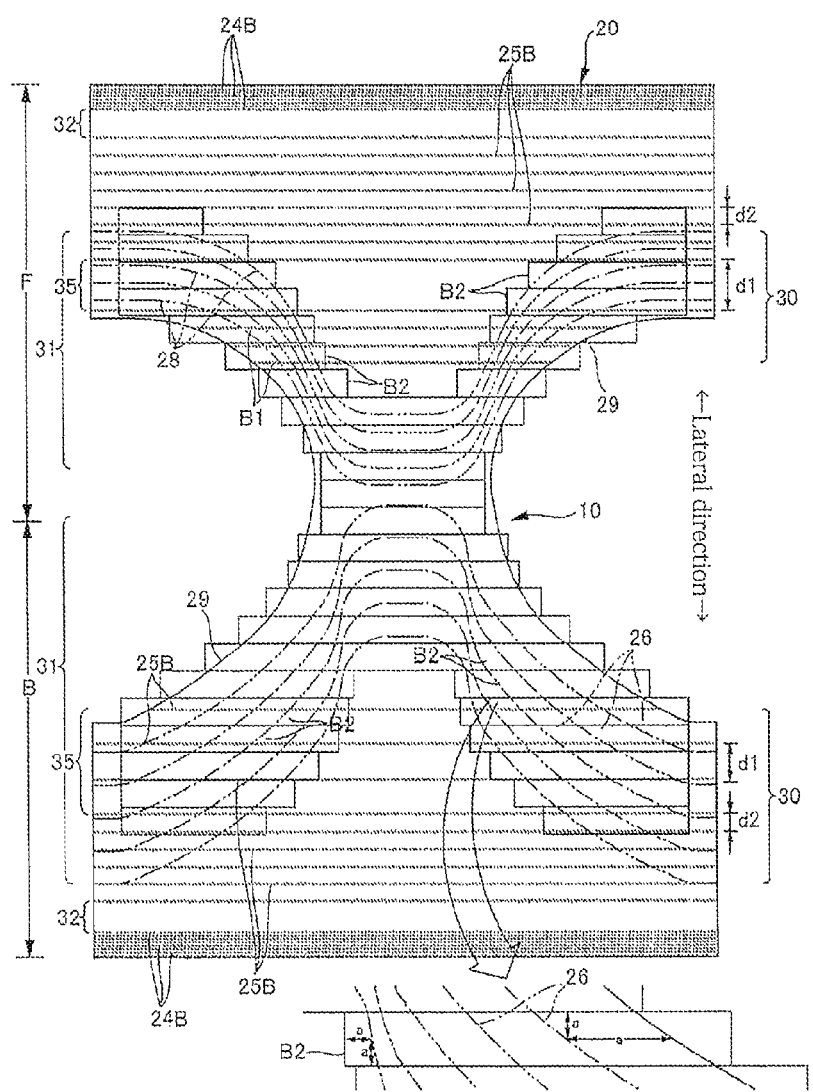
FIG. 7 is a plane view of an adhesive application pattern.

Meanwhile, the waist-portion elastic members 24, the waist-around elastic members 25 . . . , and the curved elastic members 26, . . . and 28, . . . are sandwiched between a pair of sheet layers 20A and 20B constituting the outer sheet 20. In addition, these elastic members are adhered and fixed with an adhesive to the sheet layers 20A and 20B, and the application amount of the adhesive has a great influence on flexibility of the outer sheet 20. Accordingly, as shown in FIG. 7, it is preferred to set adhesion portions B1 and B2 with the adhesive only at a placement portion of the waist-portion elastic members 24 and a neighboring portion thereof, a placement portion of the waist-around elastic members 25 . . . and a neighboring portion thereof, and placement portions of the curved elastic members 26, . . . and 28, . . . and portions at a predetermined distance a or less in vertical and horizontal sides (normally ±25 mm or less, more preferably ±10 mm or less, in particular preferably ±5 mm or less) from the placement portions, and it is preferred that no adhesive is applied to between the two sheets in portions other than the foregoing portions. As in the foregoing, minimizing the adhesive-applied portions makes it possible to significantly suppress hardening of the sheets due to application of the adhesive. In addition, when the decrease is combined with the foregoing locally increased intervals between the waist-around elastic members 25 . . . , it is possible to obtain more improvement in flexibility than can be expected.

FIG. 7 shows the hot-melt adhesive application portions B1 and B2 in the process of manufacture. The curved elastic members 26, . . . and 28, . . . are not yet cut at the positions crossing over the inner body 10 as shown by two-dot chain lines. Adhesives B1 and B2 for fixing the waist-portion elastic members 24 and the waist-around elastic members 25 . . . to the both sheet layers 20A and 20B, are virtually applied only to the placement portions of the elastic members 24 and 25 and neighboring portions thereof. This application of the adhesives can be realized by applying the adhesives to outer peripheral surfaces of and then sandwiching the elastic members 24 and 25 between the both sheet layers 20A and 20B. Such application of the adhesives to the outer peripheral surfaces of the elastic members 24 and 25 can be performed using SureWrap® Nozzles manufactured by Nordson K.K.

Meanwhile, the adhesive for fixing the curved elastic members 26, . . . and 28, . . . to the both sheet layers 20A and 20B is applied only to placement portions of the curved elastic members 26, . . . and 28, . . . and portions at the predetermined distance a or less in vertical and horizontal sides from the placement portions, over the entire longitudinal side of the curved elastic members 26, . . . and 28, . . . by aligning the rectangular adhesive application portions B2 in a staircase pattern along the curving direction of the curved elastic members 26, . . . and 28, . . . . This application of the adhesives can be performed by, in a normal mode of the application process where the horizontal side of the sheet layers 20A and 20B (width of the diaper) is made along a line MD direction (flow direction), aligning a plurality of slot application nozzles in a line CD direction (orthogonal to the MD direction) and applying the adhesives independently and intermittently from the nozzles.

(Example of Structure of Inner Body)

The inner body 10 is structured such that the absorbent body 13 intervenes between a liquid pervious face sheet 11 made of unwoven fabric or the like and a liquid impervious underside sheet 12 made of polyethylene or the like, as shown in FIGS. 4 to 6. The inner body 10 is intended to absorb and retain an excretory fluid passing through the face sheet 11.

The liquid pervious face sheet 11 covering the face side (contacting the skin of a wearer) of the absorbent body 13 may preferably be a porous or nonporous unwoven fabric or a porous plastic sheet, or the like. Material fibers for the unwoven fabric may be synthetic fibers based on olefin such as polyethylene and polypropylene, polyester, polyamide, or the like, regenerated fibers such as rayon and cupra, natural fibers such as cotton or the like. Further, the unwoven fabric may be obtained by an appropriate processing method such as a spun lace method, a spunbonding method, a thermal bonding method, a melt-blown method, and a needle punching method. Among the foregoing methods, the spun lace method is excellent in providing flexibility and drape property, and the thermal bonding method is excellent in providing high bulk and softness. If the liquid pervious face sheet 11 is formed with a large number of through-holes, the absorbent body 13 can rapidly absorb urine or the like and provide an excellent dry feel. The liquid pervious face sheet 11 extends over the side edge portions of the absorbent body 13 and reaches the underside of the absorbent body 13.

The liquid impervious underside sheet 12 covering the underside (not contacting the skin of a wearer) of the absorbent body 13 may be a liquid impervious plastic sheet made of polyethylene or polypropylene. In recent years, such a liquid impervious plastic sheet preferably has a moisture-penetration property for prevention of stuffiness. This water-proof and moisture-penetration sheet is a microporous sheet obtained by fusing and kneading an inorganic filling agent into an olefin resin such as polyethylene or polypropylene, for example, to form a sheet, and then stretching the sheet in a uniaxial or biaxial direction.

The absorbent body 13 may be formed by preparing a publicly-known base material, for example, an accumulated body of pulp fibers, an assembly of filaments of cellulose acetate or the like, or an unwoven fabric, and mixing or fixing high-absorbent polymers as necessary to the base material. In the illustrated example, the absorbent body 13 is configured to have flat planes and an approximately square shape, and have a width that does not give a wearer a stiff feeling when the absorbent body 13 is in contact with the crotch of the wearer. The absorbent body 13 can be covered by a package sheet 14 with a liquid pervious property and a liquid retaining property that is made of crepe paper or the like, as necessary for keeping the shape and holding the polymers. The absorbent body 13 may be formed in a rectangular shape as illustrated, or may be formed in a shape of an hourglass (partly narrowed shape) in which the crotch portion is narrower than the back and ventral sides.

The inner body 10 preferably has at both side portions thereof three dimensional gathers BS that fit the legs of a wearer. The three dimensional gathers BS are formed by a gather unwoven fabric 15. As shown in FIGS. 5 and 6, the gather unwoven fabric preferably is a folded and doubled unwoven fabric, which is adhered to the absorbent body 13 so as to cover from above the side edge portions of the absorbent body 13 already covered by the liquid pervious face sheet 11, and extend to the underside of the absorbent body 13. More specifically, the gather unwoven fabric 15 is adhered with a hot-melt adhesive or the like to a zone ranging from the laterally intermediate position to the underside of the absorbent body 13, except for the portion at which the three dimensional gathers BS are formed, at the longitudinally intermediate portion of the diaper 1. Meanwhile, the gather unwoven fabric 15 is adhered to a zone ranging from a section between the laterally intermediate position and one end edge to the underside of the absorbent body 13, at the longitudinally front and back ends of the inner body 10. In addition, the portion of the gather unwoven fabric 15 with the three dimensional gathers BS are folded at the upper surface portion of the absorbent body 13 and adhered with a hot-melt adhesive or the like.

A plurality of thread-like resilient and elastic members 16, 16, . . . is provided within the gather unwoven fabric 15 formed by the double-sheet unwoven fabric at a standing leading portion. The thread-like resilient and elastic members 16, 16, . . . are intended to form the three-dimensional gathers BS by raising unwoven fabric portions projected from the absorbent body side edge portions by a resilient and elastic force, as shown by two-dot chain lines in a diagram of a product state of FIG. 5.

The liquid impervious underside sheet 12 enters into the double-sheet gather unwoven fabric 15, and constitutes a leak-proof wall at the lower end of the three dimensional gathers BS, as shown in FIG. 5. The liquid impervious underside sheet 12 desirably uses an opaque material so as not to allow brown colors of stool, urine, and the like to be seen through. The liquid impervious underside sheet 12 can preferably be made opaque using a material formed by mixing into plastic, pigments such as calcium carbonate, titanium oxide, zinc oxide, white carbon, clay, talc, and barium sulfate, and a filling agent, and then shaping the plastic in a sheet.

The thread-like resilient and elastic members 16 can utilize commonly used materials such as styrene rubber, olefin rubber, urethane rubber, ester rubber, polyurethane, polyethylene, polystyrene, styrene butadiene, silicon, and polyester. In addition, to make the thread-like resilient and elastic members 16 hard to see through from the outside, the thread-like resilient and elastic members 16 preferably have a fineness of 925 dtex or less, and are arranged under a tension of 150 to 350% at intervals of 7.0 mm or less therebetween. Instead of the thread-like resilient and elastic members, tape-like resilient and elastic members with a certain level of width may be used.

As in the liquid pervious face sheet 11, material fibers for the gather unwoven fabric 15 may be synthetic fibers based on olefin such as polyethylene and polypropylene, polyester, amide, or the like, regenerated fibers such as rayon and cupra, natural fibers such as cotton or the like. The gather unwoven fabric 15 may be an unwoven fabric obtained by an appropriate processing method such as a spunbonding method, a thermal bonding method, a melt-blown method, and a needle punching method. In particular, the unwoven fabric favorably has a decreased basis weight and excellent air permeability for prevention of stuffiness. Further, the gather unwoven fabric 15 desirably is a water-repellent unwoven fabric with a coating of a water-repellent agent based on silicon, paraffin metal, alkyl chromic chloride in order to prevent passage of urine or the like, avoid rash, and enhance a skin feeling (dry feeling).

(Fixation of Inner Body and Outer Sheet)

The inner body 10 and the outer sheet 20 are fixed together in a characteristic structure. As shown in FIG. 3, in a view of the diaper in an open state, the outer sheet 20 and the inner body 10 are not fixed in vertical zones of 80% or more (an entire vertical zone in the illustrated example) of intersecting portions 70 (dot-patterned portions encircled by two-dot chain lines in FIG. 3) at which a smaller angle θ formed by the curved elastic members 26, . . . and 28, . . . intersecting with the vertical direction is 600 or less, whereas the outer sheet 20 and the inner body 10 are fixed together by joint means such as a hot-melt adhesive at other sections 80, 81, and 82. Accordingly, the curved elastic members 26, . . . and 28, . . . hardly or do not exert contraction force on the side portions of the inner body 10, and as a result, the diaper has thickness and hardness at the overlapping area of the curved elastic members 26, . . . and 28, . . . and the both side portions of the inner body 10 that are in the same level as those at the surrounding area. This makes the inner body 10 less prone to cause lateral wrinkles on the internal surface. In addition, as far as the outer sheet 20 and the inner body 10 are fixed together in the vertical zones of 80% or more of the intersecting portions 70, the inner body 10 and the outer sheet 20 may be continuously fixed in the entirety as in the illustrated example, may not be fixed at a part of the intersecting portions, or may be intermittently fixed at the intersecting portions.

Meanwhile, as long as unfixed sections 71 are provided in zones containing the intersecting portions 70 as described above, the fixed section between the outer sheet 20 and the inner body 10 needs to be smaller in the vertical zones corresponding to the intersecting portions 70. Accordingly, it is desired that, in a view of the diaper in an open state, non-stretched sections with no elastic members are provided on a lateral central side with respect to the intersecting portions 70 in the vertical zones and the non-stretched sections are set as fixed sections 80 between the outer sheet 20 and the inner body 10; and non-stretched sections with no elastic members are provided ranging from laterally outer sides with respect to laterally intermediate edges of the intersecting portions 70 to the laterally central side with respect to the intersecting portions 70 in a vertical zones corresponding to the waist sides with respect to the intersecting portions 70, and the non-stretched portions are set as fixed sections 81 between the outer sheet 20 and the inner body 10. Specifically, as in the illustrated example, it is suggested that the fixation width of the outer sheet 20 and the inner body 10 be made identical to or less than the interval between the intersecting portions 70 on both lateral sides in the vertical zones corresponding to the intersecting portions 70, and is made larger than the same on the waist sides with respect to the intersecting portions 70 (the width may be increased stepwise as in the illustrated example or may be increased continuously). This allows the inner body 10 to be more firmly fixed.

It is also suggested that the curved elastic members 26, . . . and 28, . . . be arranged at the front body part F and the back body part B; the front and back curved elastic members 26, . . . and 28, . . . not intersect one another to provide a vertical separation zone 90; also in the vertical separation zone 90, a non-stretched section with no elastic members be provided from the lateral outer sides with respect to the lateral intermediate side edges of the intersecting portions 70 to the lateral center sides with respect to the intersecting portions 70, and the non-stretched section be set as a fixed section 82 between the outer sheet 20 and the inner body 10; and the fixation width in the vertical separation zone 90 be larger than the fixation width in the vertical zone corresponding to the intersecting portions 70. This allows the inner body 10 to be further firmly fixed.

(Front and Back Retention Sheets)

As shown in FIGS. 1 and 4, front and back retention sheets 50 and 60 are provided to cover the front and back end portions of the inner body 10 attached on the internal surface of the outer sheet 20, and prevent leakage from the front and back edges of the inner body 10. For more detailed description of the illustrated embodiment, the front retention sheet 50 extends along the entire width of the internal surface of the front body part F, ranging from the internal surface of the folded portion 20C at the waist side end to a position overlapping the front end portion of the inner body 10. The back retention sheet 60 extends along the entire width of the internal surface of the back body part B, ranging from the internal surface of the folded portion 20C at the waist side end portion to a position overlapping the back end portion of the inner body 10. When the front and back retention sheets 50 and 60 are provided with small non-adhered portions along the entire width (or only at the center) of the inseam side edge portions, it is possible to prevent an adhesive from being squeezed out and allow the portions to be slightly lifted from the face sheet and serve as a leak-proof wall.

As in the illustrated mode, when the front and back retention sheets 50 and 60 are attached as separate components, there is an advantage of providing a higher degree of freedom for selection of a material, but there is also a disadvantage of increasing resources and steps required in a manufacturing process and the like. Accordingly, the folded portions 20C formed by folding back the outer sheet 20 toward the internal surface of the diaper 1 may be extended to overlap the absorbent pad 200 and form portions equivalent to the retention sheets 50 and 60.

(Unwoven Fabric Constituting Outer Sheet)

Among the unwoven fabrics constituting the outer sheet 20, at least the unwoven fabric 20B on the outermost side preferably has a torsional stiffness of 3.8 gf·cm/cm or less. The "torsional stiffness" here can be measured using KES-YN1 (manufactured by Kato Tech Co., Ltd.), and the like, and the smaller the value of the torsional stiffness is, the unwoven fabric is more flexible against torsion. In addition, if the outer sheet is formed by one sheet of unwoven fabric, the unwoven sheet is the sheet positioned on the outermost side. All of the unwoven fabrics constituting the outer sheet 20, that is, all of the unwoven fabrics including the unwoven fabrics 20A, 50, and 60 not positioned on the outermost side, desirably use the same unwoven fabric as the outermost unwoven fabric 20B (this also applies to the following descriptions). As in the foregoing, if the unwoven fabric used has a sufficiently low torsional stiffness, the entire diaper is significantly increased in flexibility, and as a result, it is possible to decrease a stiff feeling and skin troubles such as itch and rash resulting from friction with the fabric, and produce an advantage of easy wearing and removing, and the like. The effect of improvement in flexibility does not develop without a sufficiently low torsional stiffness. Such a low torsional stiffness can be realized by selecting the favorable kind of material fibers, decreasing fineness, shortening fiber length, decreasing fiber basis weight or thickness, or the like, for example.

In addition, the MIU/MMD, the ratio of mean coefficient of friction to mean deviation of MIU at the outermost unwoven fabric 20B is preferably 20 or more, in particular 25 or more. With the sufficiently large MIU/MMD ratio, the outer sheet has a favorable surface feeling, which makes it possible to add flexibility and further reduce skin troubles such as itch and rash resulting from friction with the fabric, for example. Such an MIU/MMD ratio can be achieved by decreasing fineness, applying a surface finish, or the like, for example.

In addition, the outermost unwoven fabric 20B preferably has a basis weight of 10 to 30 g/m$^2$ and a thickness T0 of 0.1 to 1.0 mm under a pressure of 0.5 g/cm$^2$, so as not to deteriorate basic functions of the outer sheet 20 (covering function, strength, and the like). More preferably, the outermost unwoven fabric 20B has a basis weight of 13 to 22 g/m$^2$ and a thickness T0 of 0.1 to 0.5 mm.

To further add flexibility, the outermost unwoven fabric 20B has a bending resistance of preferably 45 mm or less, more preferably 35 mm or less measured in accordance with JIS-L-1096 (45-degree cantilever method). Accordingly, the diaper can be particularly reduced in stuffiness and can be easily worn and removed in a further preferable manner. Such a bending resistance can be achieved by selecting the favorable kind of material fibers, changing a fiber proportion, lowering an emboss pressure, decreasing fiber basis weight and thickness, or the like, for example.

If the outer sheet 20 is improved in flexibility, the outer sheet 20 is prone to decrease in strength. Accordingly, the outermost unwoven fabric 20B favorably has a tensile strength specified in accordance with JIS-P-8113 of 40 to 120 kgf/m, in particular 60 to 100 kgf/m in the lateral direction, and 10 to 80 kgf/m, in particular 25 to 60 kgf/m in the front-back direction. In addition, the outermost unwoven fabric 20B favorably has a tear strength specified in accordance with JIS-P-8116 of 4 to 30 kgf/m, in particular 8 to 25 kgf/m in the front-back direction. The foregoing tensile strength and tear strength can be achieved by increasing the degree of entanglement of fibers, for example.

Compressive characteristics of the outermost unwoven fabric 20B are closely related to flexibility. Accordingly, as compressive characteristics, the outermost unwoven fabric 20B preferably has a compressive hardness LC of 0.3 to 1.0, in particular 0.5 to 0.9, and a compressional energy WC of 0.01 to 0.10, in particular 0.01 to 0.07, and a compressive resilience RC of 20 to 90%, in particular 25 to 70%. Such compressive hardness LC, the compressional energy WC, and the compressive resilience RC can be achieved by selecting the favorable kind of material fibers, changing a fiber proportion, decreasing fiber basis weight and thickness, or the like, for example.

For the outermost unwoven fabric 20B, there are no particular limitations in substance, structure, manufacturing method, fineness, fiber length (short fiber or filament) of material fibers, and the like. For example, the material fibers can be appropriately selected from synthetic fibers based on olefin such as polyethylene and polypropylene, polyester, and polyamide, regenerated fibers such as rayon and cupra, natural fibers such as cotton and the like. The fiber structure can be selected as appropriate from two-layer composite fiber structures such as a parallel type and a core-clad type, multi-layer composite fiber structures, non-composite fiber structures, mixed fiber structures, split fiber structures, and the like. Further, the manufacturing method can be selected as appropriate from publicly-known methods such as a spun lace method, a spunbonding method, a thermal bonding method, a melt-blown method, a needle punching method, an air-through method, and a point bonding method. For the fineness and length, the publicly-known specifications can be employed, but the fiber size is preferably 0.7 to 3 dtex, in particular 1 to 2.5 dtex.

(Testing Examples)

Various kinds of unwoven fabric samples were prepared to conduct various tests and measurements. Material fibers for the sample unwoven fabrics are all continuous fibers (long fibers) as understood from the manufacturing methods. The fibers were confirmed as being almost the same in diameter (about 0.15 to 0.25 μm) by microscope observation. The unwoven fabric samples were subjected to fluff testing using a friction block covered with a dry, white cotton cloth, in conformance with Gakushin (Japan Society for the Promotion of Science) type friction testing specified by JISK6404-16. The unwoven fabric samples were observed for fluffy state under a microscope, and were evaluated by a five-point scale using evaluation criteria: 1; raised fibers have a height of 1 mm or less; 2; raised fibers have a height of 2 mm or less; 3; raised fibers have a height of 3 mm or less; 4; fabric has a small amount of fluff, and raised fibers have a height of 3 mm or more; and 5: fabric has a large amount of fluff on the entire surface, and raised fibers have a height of 3 mm or more. The ratio MIU/MMD was calculated by formula (MIU (in the lateral direction)+ MIU (in the longitudinal direction)/(MMD (in the lateral direction)+MMD (in the longitudinal direction). Other conditions not described here (such as usage amount of an adhesive or the like) were common in all the samples.

Further, the sample unwoven fabrics were used as constituent unwoven fabrics 20A, 20B, 51, and 61 of the outer sheet 20 in an underpants-type disposable diaper that have almost the same structure as that shown in FIGS. 1 to 11 (in which no bending fit portion or intergluteal cleft-portion elastic members are provided and the intervals between the curved elastic members are almost the same between the front body part and the back body part), to prepare an underpants-type disposable diaper similar to that shown in the foregoing drawings, and perform sensory evaluation on the diaper for flexibility (evaluation criteria: ⊙: excellent, Δ: acceptable, ×: stiff).

Figure 13:
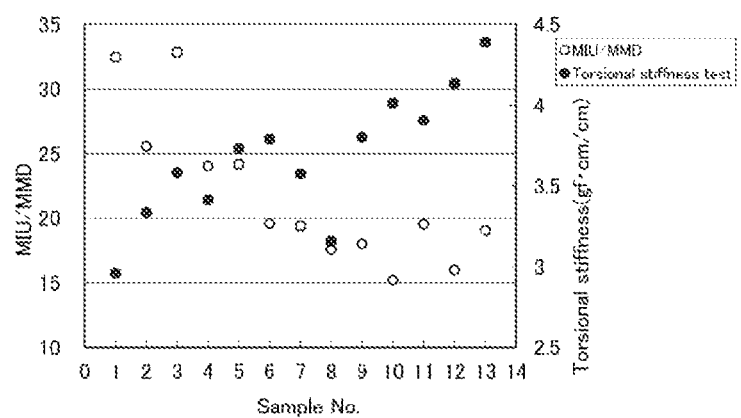
FIG. 13 is a graph showing results of testing for MIU/MMD and torsional stiffness.
Figure 14:
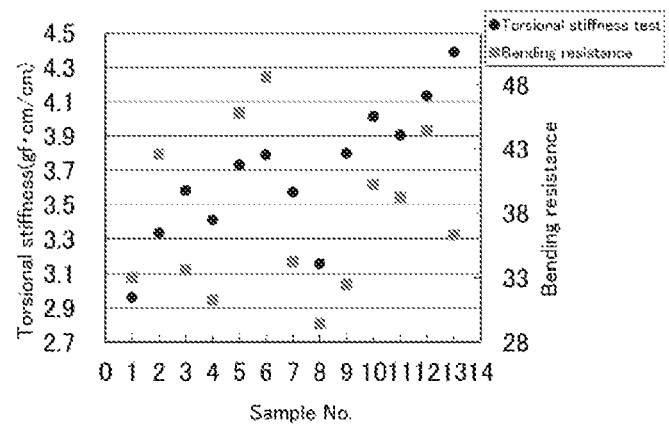
FIG. 14 is a graph showing results of testing for torsional stiffness and bending resistance.
Figure 15:
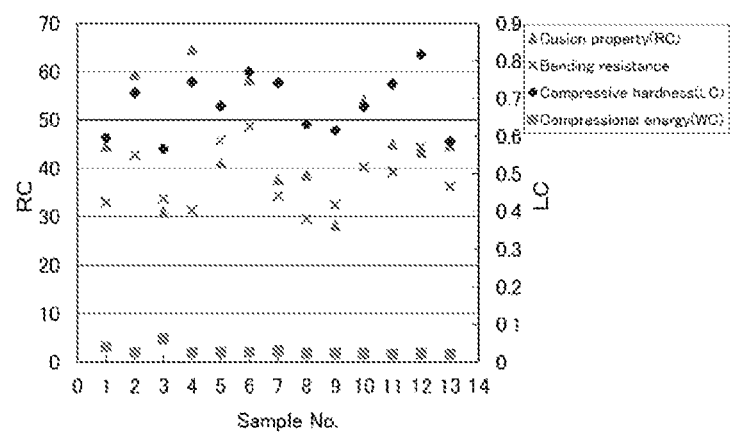
FIG. 15 is a graph showing results of testing for compressive hardness LC, compressional energy WC, compressive resilience RC, and bending resistance.

Table 1 shows results of the foregoing testing. In addition, FIGS. 13 to 15 show some graphs. As apparent from these results, samples 1 to 9 were excellent in flexibility and suited for a diaper. Among these samples, the samples with a MIU/MMD rate of 20 or more were given high ratings in sensory evaluation. Further, among the samples with high ratings, the samples with a bending resistance of 35 mm or less were given higher ratings in sensory evaluation.

TABLE 1

| Sample No. | | 1 | 2 | 3 | 4 | 5 | 6 | 7 |
|---|---|---|---|---|---|---|---|---|
| Fiber substance and structure | | PP (single) | PP/PE (clad/core) | PP (single) | PP copolymer (single) | PP (single) | PP/PE (clad/core) | PP/PE (clad/core) |
| Basis weight (g/m²) | | 18.0 | 18.0 | 18.0 | 15.0 | 15.2 | 18.0 | 19.4 |
| Thickness (mm) | | 0.12 | 0.18 | 0.21 | 0.10 | 0.18 | 0.19 | 0.09 |
| Manufacturing method | | Spun bonding | Spun bonding | Spun bonding | Spun bonding | Spun bonding | Spun bonding | Spun bonding |
| Tensile strength | Lateral direction | 3.36 | 4.00 | 3.44 | 2.79 | 3.79 | 3.41 | 4.54 |
| | Longitudinal direction | 1.70 | 2.00 | 1.71 | 1.29 | 1.58 | 1.59 | 2.83 |
| Tear strength | Longitudinal direction | 0.580 | 0.946 | 0.575 | 0.475 | 0.582 | 0.668 | 0.970 |
| Fluff | | 4 | 1 | 3 | 4 | Not tested | 1 | Not tested |
| Mean coefficient of friction (MIU) | Lateral direction | 0.171 | 0.172 | 0.200 | 0.22 | 0.041 | 0.149 | 0.074 |
| | Longitudinal direction | 0.183 | 0.186 | 0.204 | 0.222 | 0.046 | 0.162 | 0.081 |
| Mean deviation of MIU (MMD) | Lateral direction | 0.0052 | 0.0065 | 0.0056 | 0.0078 | 0.001 | 0.0074 | 0.004 |
| | Longitudinal direction | 0.0057 | 0.0075 | 0.0067 | 0.0106 | 0.002 | 0.0085 | 0.004 |
| MIU/MMD | | 32.48 | 25.57 | 32.85 | 24.02 | 24.17 | 19.56 | 19.38 |
| Compressive hardness (LC) | | 0.595 | 0.715 | 0.566 | 0.744 | 0.680 | 0.771 | 0.741 |
| Compressional energy (WC) | | 0.04 | 0.026 | 0.062 | 0.025 | 0.027 | 0.026 | 0.030 |
| Cushion property (RC) | | 44.59 | 59.34 | 30.88 | 64.66 | 41.06 | 58.34 | 37.63 |
| Bending resistance | Lateral direction | 33.0 | 42.6 | 33.6 | 31.3 | 45.8 | 48.6 | 34.2 |
| torsional stiffness | Lateral direction | 2.9610 | 3.3349 | 3.5810 | 3.4118 | 3.7307 | 3.7896 | 3.5733 |
| Sensory evaluation | | ⊙ | ⊙ | ⊙ | ○ | ○ | Δ | Δ |

TABLE 1-continued

| Sample No. | | 8 | 9 | 10 | 11 | 12 | 13 |
|---|---|---|---|---|---|---|---|
| Fiber substance and structure | | PP copolymer (single) | PP/PE (clad/core) | PP (single) | PP (single) | PP/PE (clad/core) | PP (single) |
| Basis weight (g/m²) | | 15.4 | 19.0 | 14.7 | 15.0 | 20.0 | 20.0 |
| Thickness (mm) | | 0.10 | 0.12 | 0.11 | 0.07 | 0.10 | 0.14 |
| Manufacturing method | | Spun bonding | Spun bonding | SMMS | SS | Spun bonding | Spun bonding |
| Tensile strength | Lateral direction | 2.89 | 3.45 | 3.00 | 3.70 | 4.217 | 5.18 |
| | Longitudinal direction | 1.35 | 1.54 | 1.00 | 1.92 | 1.932 | 2.34 |
| Tear strength | Longitudinal direction | 0.511 | 0.618 | 0.575 | 0.559 | 0.862 | 0.738 |
| Fluff | | Not tested | Not tested | 1 | Not tested | 1 | 5 |
| Mean coefficient of friction (MIU) | Lateral direction | 0.218 | 0.07 | 0.037 | 0.041 | 0.16 | 0.184 |
| | Longitudinal direction | 0.224 | 0.074 | 0.039 | 0.041 | 0.187 | 0.206 |
| Mean deviation of MIU (MMD) | Lateral direction | 0.0118 | 0.004 | 0.0023 | 0.002 | 0.0091 | 0.0089 |
| | Longitudinal direction | 0.0134 | 0.004 | 0.0027 | 0.0022 | 0.0126 | 0.0116 |
| MIU/MMD | | 17.54 | 18.00 | 15.20 | 19.52 | 15.99 | 19.02 |
| Compressive hardness (LC) | | 0.631 | 0.615 | 0.678 | 0.738 | 0.817 | 0.585 |
| Compressional energy (WC) | | 0.024 | 0.024 | 0.023 | 0.021 | 0.023 | 0.021 |
| Cushion property (RC) | | 38.59 | 28.18 | 54.12 | 45.02 | 43.24 | 44.74 |
| Bending resistance | Lateral direction | 29.4 | 32.5 | 40.2 | 39.2 | 44.4 | 36.3 |
| torsional stiffness | Lateral direction | 3.1552 | 3.7993 | 4.0127 | 3.9062 | 4.1348 | 4.3888 |
| Sensory evaluation | | Δ | Δ | x | x | x | x |

INDUSTRIAL APPLICABILITY

The present invention can be used in underpants-type disposable diapers as in the foregoing example.

BRIEF DESCRIPTION OF NUMERALS

1 . . . Underpants-type disposable diaper, 10 . . . Inner body, 11 . . . Liquid pervious face sheet, 12 . . . Liquid impervious underside sheet, 13 . . . Absorbent body, 14 . . . Package sheet, 15 . . . Gather nonwoven fabric, 16 . . . Thread-like resilient and elastic member, 20 . . . Outer sheet, 21, 22 . . . Side portion joint edge, 24 . . . Waist-portion elastic member, 25 . . . Waist-around elastic member, 26 . . . Back-side curved elastic member, 28 . . . Ventral-side curved elastic member, 29 . . . Leg-encircling line, 20C . . . Outer sheet folded portion, 70 . . . Intersecting portion, 71 . . . Unfixed section, 80, 81, 82 . . . Fixed section, θ . . . Vertically intersecting angle, F . . . Front body part, B . . . Back body part

The invention claimed is:

1. An underpants-type disposable diaper, comprising: an outer sheet forming a front body part and a back body part; and an inner body having a perimeter and including an absorbent body and fixed to an internal surface of the outer sheet, the front and back body parts of the outer sheet being joined to each other at respective side portions thereof to form a waist opening and a pair of leg openings, wherein
   the outer sheet of the back body part has an intergluteal cleft facing portion located at a lateral center portion and side areas located laterally to the right and left of the intergluteal cleft facing portion, respectively,
   a portion of each of the side areas, which is adjacent to the intergluteal cleft facing portion and within the boundaries of the inner body perimeter, is located so as to be apart from an edge of the outer sheet of the back body part toward a lateral center side,
   the outer sheet of the back body part has an elongated intergluteal cleft portion elastic member extended laterally over the intergluteal cleft facing portion and within the boundaries of the inner body perimeter,
   the intergluteal cleft portion elastic member is cut at the portion of each of the side areas, which is adjacent to the intergluteal cleft facing portion,
   the back body part has at the intergluteal cleft facing portion a bending fit portion which is bent so as to enter into the intergluteal cleft of a wearer by the intergluteal cleft portion elastic member acting a contraction force on the intergluteal cleft facing portion,
   the outer sheet has at each of the front and back body parts a lifting elastic member which exerts a contraction force of a vertical component to lift a crotch portion toward a waist side,
   each lifting elastic member is cut at the portion of each of the side areas, which is adjacent to the intergluteal cleft facing portion and within the boundaries of the inner body perimeter.

2. The underpants-type disposable diaper according to claim 1, wherein
   a part of the intergluteal cleft facing portion under the action of the contraction force of the intergluteal cleft portion elastic member is shaped so as to be wider in a backward direction from a front end to a longitudinal middle of the intergluteal cleft facing portion, and to be narrower in the backward direction from the longitudinal middle to a further back side of the intergluteal cleft facing portion.

3. The underpants-type disposable diaper according to claim 2, wherein
   a groove or a slit is formed in the absorbent body so as to follow the intergluteal cleft of a wearer, and the bending fit portion is formed with the groove or the slit as a folding line.

4. The underpants-type disposable diaper according to claim 2, wherein
both lifting elastic members comprise an elongated curved elastic member, which is fixed, on each of the front and back body parts of the outer sheet, so as to curve and extend toward the other body part while running from the side portions towards the lateral center, in a state of being stretched in a direction of extension of the elongated curved elastic member at a predetermined extension ratio.

5. The underpants-type disposable diaper according to claim 1, wherein
a groove or a slit is formed in the absorbent body so as to follow the intergluteal cleft of a wearer, and the bending fit portion is formed with the groove or the slit as a folding line.

6. The underpants-type disposable diaper according to claim 5, wherein
both lifting elastic members comprise an elongated curved elastic member, which is fixed, on each of the front and back body parts of the outer sheet, so as to curve and extend toward the other body part while running from the side portions towards the lateral center, in a state of being stretched in a direction of extension of the elongated curved elastic member at a predetermined extension ratio.

7. The underpants-type disposable diaper according to claim 1, wherein
both lifting elastic members comprise an elongated curved elastic member, which is fixed, on each of the front and back body parts of the outer sheet, so as to curve and extend toward the other body part while running from the side portions towards the lateral center, in a state of being stretched in a direction of extension of the elongated curved elastic member at a predetermined extension ratio.

8. The underpants-type disposable diaper according to claim 7, wherein
a plurality of curved elastic members is aligned with predetermined intervals therebetween in the front and back body parts, and
at portions on lateral outer sides with respect to side edges of the inner body, vertical intervals between the curved elastic members at the back body part are larger than vertical intervals between the curved elastic members at the front body part.

9. The underpants-type disposable diaper according to claim 8, wherein
on each of the front and back body parts of the outer sheet, a plurality of elongated waist-portion elastic members laterally extending is fixed at an edge portion of the waist opening at vertical intervals therebetween in a state of being laterally stretched at a predetermined extension ratio, and a plurality of elongated waist-around elastic members laterally extending is fixed in a section, at a longitudinally intermediate portion side with respect to the waist-portion elastic members, at vertical intervals therebetween in a state of being laterally stretched at a predetermined extension ratio.

10. The underpants-type disposable diaper according to claim 9, wherein
the outer sheet is formed by bonding together a plurality of sheets of nonwoven fabric with an adhesive at least at portions with the waist-portion elastic members, the waist-around elastic members, and the curved elastic members, and the waist-portion elastic members, the waist-around elastic members, and the curved elastic members are sandwiched and fixed between the nonwoven fabric sheets,
a basis weight of the outer sheet is 30 to 75 $g/m^2$,
the waist-portion elastic members at the front and back body parts are 470 to 1.240 dtex in fineness, are 5 to 10 in number, have intervals of 0 to 5 mm therebetween, and have an extension ratio of 200 to 350% in a fixed state,
the waist-around portion elastic members at the front and back body parts are 470 to 1,240 dtex in fineness, are 6 to 26 in number, have intervals 10 to 40 mm therebetween, and have an extension ratio of 200 to 350% in a fixed state,
the curved elastic members at the front body part are 620 to 1,240 dtex in fineness, are 3 to 10 in number, have intervals 10 to 35 mm therebetween, and have an extension ratio of 230 to 380% in a fixed state that is higher than an extension ratio of the curved elastic members at the back body part, and
the curved elastic members at the back body part are 620 to 1.240 dtex in fineness, are 3 to 10 in number, have intervals 10 to 35 mm therebetween, and have an extension ratio of 200 to 350% in a fixed state.

* * * * *